United States Patent [19]

Abou-Gharbia et al.

[11] Patent Number: 4,833,249

[45] Date of Patent: May 23, 1989

[54] ISOTHIAZOLONE 1,1-DIOXIDE DERIVATIVES WITH PSYCHOTROPIC ACTIVITY

[75] Inventors: Magid A. Abou-Gharbia, Wilmington, Del.; Guy A. Schiehser, Malvern; Usha R. Patel, Audubon, both of Pa.

[73] Assignee: American Home Products Corporation, New York, N.Y.

[21] Appl. No.: 22,197

[22] Filed: Mar. 5, 1987

[51] Int. Cl.$^4$ .................. C07D 417/16; C07D 521/00
[52] U.S. Cl. ...................................... 546/270; 544/238; 544/320; 544/321; 544/323; 544/324; 544/327; 544/331; 544/332; 544/336; 544/353; 544/354; 544/356; 544/405; 544/408; 544/409; 546/153; 546/175; 546/193; 546/194; 546/198; 546/200; 546/209
[58] Field of Search ........................................ 546/270

[56] References Cited

U.S. PATENT DOCUMENTS

| | | |
|---|---|---|
| 4,550,168 | 10/1985 | Welter et al. .................... 546/270 |
| 4,562,255 | 12/1985 | Freed et al. ...................... 546/270 |
| 4,711,961 | 12/1987 | Welter et al. .................... 546/270 |

OTHER PUBLICATIONS

Chiyomaru et al., "Chemical Abstracts", vol. 78(25), 1973, Col. 155417a.

Primary Examiner—Glennon H. Hollrah
Assistant Examiner—James H. Turnipseed
Attorney, Agent, or Firm—George Tarnowski

[57] ABSTRACT

There are disclosed compounds of the formula

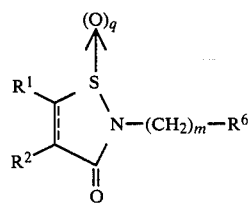

wherein
$R^1$ and $R^2$ are each, independently, hydrogen, lower alkyl, aryl or halo, or $R^1$ and $R^2$ taken together represent

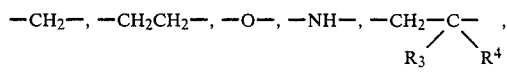

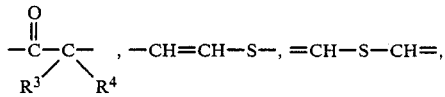

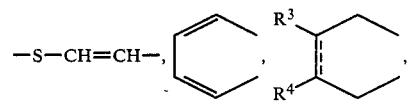

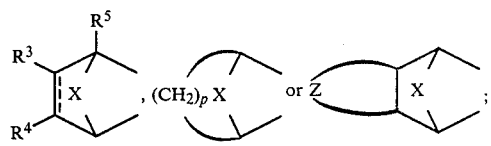

where the dotted lines represent optional double bonds;
$R^3$, $R^4$ and $R^5$ are each, independently, hydrogen, lower alkyl, aryl or halo;
$R^6$ is 2-pyridinyl, 2-pyrazinyl, 2-quinolyl, 2-quinoxalinyl or any of the foregoing $R^6$ moieties substituted by lower alkyl, lower alkoxy, trifluoromethyl, cyano, nitro or halo; or
$R^6$ is

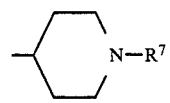

wherein $R^7$ is phenyl, 2-pyridinyl, 2-pyrimidinyl, 3-pyridazinyl or 2-pyrazinyl or any of the foregoing $R^7$ moieties substituted by lower alkyl, lower alkoxy, halo, cyano, trifluoromethyl or nitro;
Z is —(CH$_2$)$_n$—, —O—, or

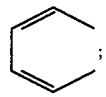

X is lower alkylene, vinylene, O or NH;
m is 1–5;
n is 0–4;
p is 1–4;
q is 1–2;
and the pharmaceutically acceptable salts thereof, and their use as antipsychotic/anxiolytic agents having a low liability for extrapyramidal side effects.

4 Claims, No Drawings

ISOTHIAZOLONE 1,1-DIOXIDE DERIVATIVES WITH PSYCHOTROPIC ACTIVITY

This invention relates to novel compounds having antipsychotic activity and being characterized by the general formula

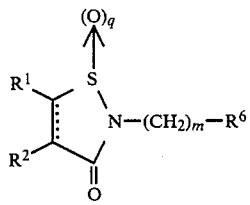

wherein $R^1$ and $R^2$ are each, independently, hydrogen, lower alkyl, aryl or halo, or $R^1$ and $R^2$ taken together represent

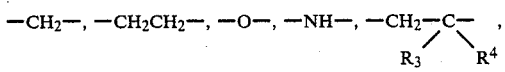

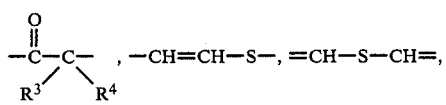

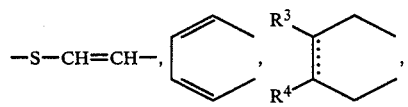

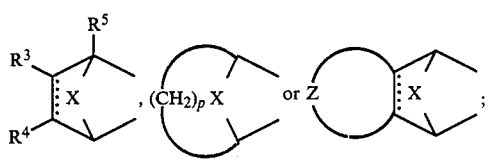

where the dotted lines represent optional double bonds;

$R^3$, $R^4$ and $R^5$ are each, independently, hydrogen, lower alkyl, aryl or halo;

$R^6$ is 2-pyridinyl, 2-pyrazinyl, 2-quinolyl, 2-quinoxalinyl or any of the foregoing $R^6$ moieties substituted by lower alkyl, lower alkoxy, trifluoromethyl, cyano, nitro or halo; or $R^6$ is

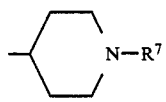

wherein $R^7$ is phenyl, 2-pyridinyl, 2-pyrimidinyl, 3-pyridazinyl or 2-pyrazinyl or any of the foregoing $R^7$ moieties substituted by lower alkyl, lower alkoxy, halo, cyano, trifluoromethyl or nitro;

Z is -$(CH_2)_n$-, -O-, or

X is lower alkylene, vinylene, O or NH;

m is 1–5;

n is 0–4;

p is 1–4;

q is 1–2;

and the pharmaceutically acceptable salts thereof.

The term "lower alkyl" refers to moieties having 1–6 carbon atoms in the carbon chain. The term "lower alkylene" refers to moieties having 1–4 carbon atoms in the carbon chain. The term "aryl" refers to moieties having 6–12 carbon atoms. The term "halo" refers to fluoro, chloro and bromo.

The compounds of the invention can form pharmacologically acceptable salts from pharmacologically acceptable organic and inorganic acids such as hydrochloric, hydrobromic, sulfuric, phosphoric, nitric, maleic, fumaric, benzoic, ascorbic, pamoic, succinic, methanesulfonic, acetic, propionic, tartric, citric, lactic, malic, mandelic, cinnamic, palmitic, itaconic and benzenesulfonic.

The compounds of the invention may be prepared by a variety of synthetic routes using conventional methods. For example, 3-isothiazolone 1,1-dioxide can be reacted with an appropriate diene to yield a precursor which when reacted with a suitable heterocyclic alkyl halide affords the desired product:

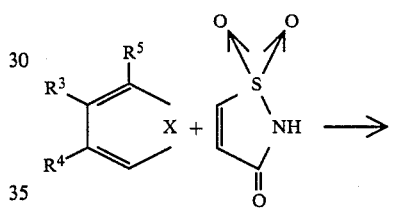

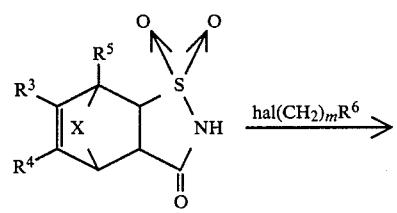

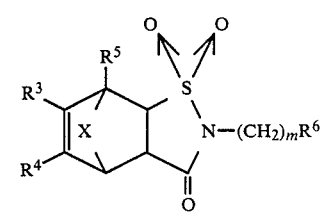

Compounds in which $R^6$ is an N-heterocyclic substituted piperidine moiety may be prepared by the following reaction scheme, where the starting pyridine derivative is prepared according to the above-outline preparative scheme:

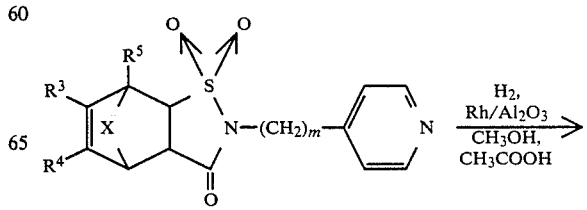

-continued

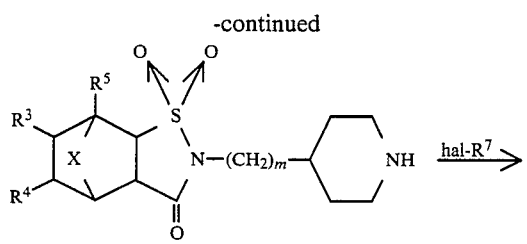

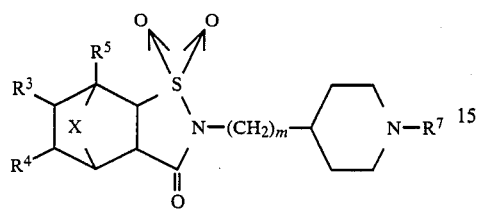

In the above reaction sequence, the reduction of the pyridine is carried out with hydrogen in methanol in the presence of 5% rhodium/Al$_2$O$_3$ and glacial acetic acid. The reduced pyridine intermediate is then alkylated with the appropriate haloheterocycle in dimethylformamide in the presence of triethylamine or cesium carbonate.

In the above sequences, R$^3$, R$^4$, R$^5$, R$^6$, R$^7$, X and m are as defined hereinbefore and hal is a halo atom, such as chloro or bromo. Compounds in which R$^1$ and R$^2$ taken together represent

—CH═CH—S—, ═CH—S—CH═,

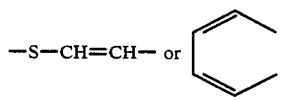

can be prepared in like manner using an appropriate benzoisothiazolone 1,1-dioxide or thienoisothiazolone 1,1-dioxide as the starting material.

Compounds of the invention in which R$^1$ and R$^2$ taken together represent the moiety

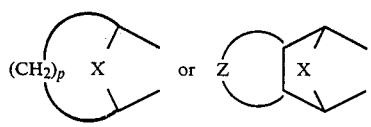

are prepared via the Diels-Alder addition outlined above, using a diene of appropriate ring size and degree of unsaturation. The following examples are illustrative:

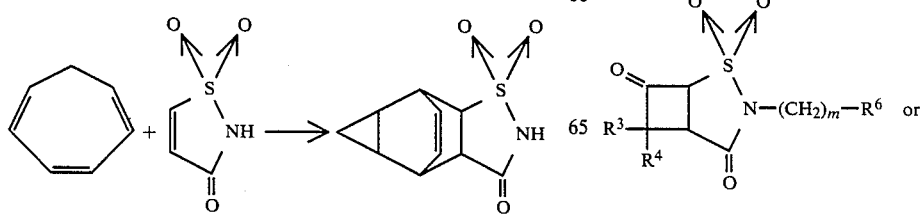

-continued

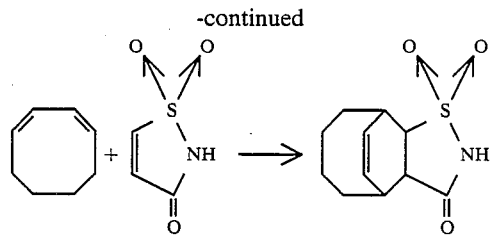

If instead of a Diels-Alder addition, the 3-isothiazolone 1,1-dioxide is subjected to epoxidation or carbene insertion, the corresponding final products can be obtained:

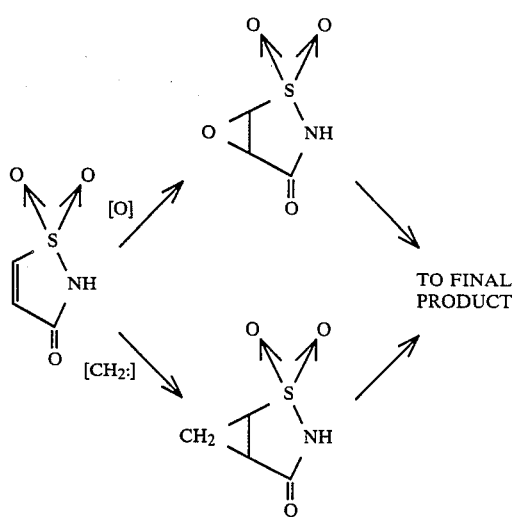

In an alternative preparative sequence, the 3-isothiazolone 1,1-dioxide can first be reacted with an appropriate heterocyclic alkyl halide to yield the following intermediate:

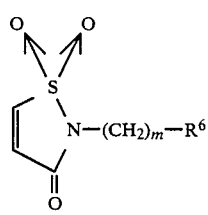

which can then be further reacted with appropriate reactants to yield desired final products. Thus, Diels-Alder addition of a diene, epoxidation or carbene insertion will yield the appropriate final product.

Compounds of the invention having the formula

-continued

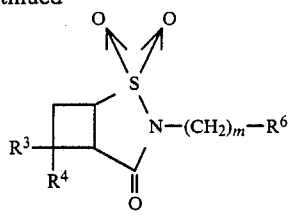

wherein $R^3$ and $R^4$ are as defined hereinbefore can be prepared by the same sequences as have been outlined, reacting a suitable ketene with the 3-isothiazolone 1,1-dioxide to obtain the desired intermediate, e.g.:

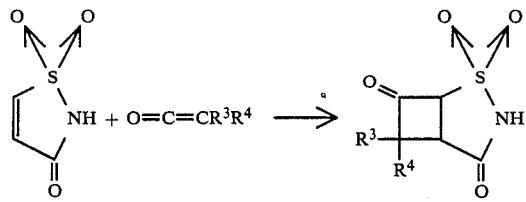

wherein $R^3$ and $R^4$ are as defined hereinbefore.

The saturated analogs of the compounds discussed above can be prepared by hydrogenating the intermediates or the final products using hydrogen and Pd/C as a catalyst.

Of course, other methods of preparation, which will occur to those skilled in the art, may also be employed to prepare the compounds of the invention.

The starting materials used in the above-described preparative routes are commercially available, or can be made according to procedures taught in the chemical literature.

The compounds of the invention may exist either in the form of the free base or the pharmacologically acceptable salts. Methods for converting one such form to another will be obvious to one skilled in the chemical arts.

The compounds of the invention display a pharmacological profile like that of the compound buspirone (8-[4-[4-(2-pyrimidinyl)-1-piperazinyl]butyl]-8-azaspiro[4.5]decane-7,9-dione). The latter compound has demonstrated preclinical activity in antipsychotic paradigms and has also displayed a unique clinical anxioselective profile, whereby its efficacy in the treatment of anxiety neuroses is comparable to the benzodiazepine diazepam but without the benzodiazepine-related side effects. The clinically effective anxiolytic doses of the benzodiazepines produce such undesirable side effects as ataxia, muscle relaxation and sedation. Additionally, most chronically used antipsychotic drugs, cause extrapyramidal side effects, such as pseudoparkinsonism, tardive dyskinesia and the like. Ideally, treatment of psychoses and anxiety should be free of any undesirable side effects. The compounds of the invention, in a manner similar to buspirone, display antipsychotic activity without or with minimal side effects. Moreover, based on their buspirone-like profile, the compounds of the invention can be considered of clinical value in treating anxiety neuroses.

When employed as anxiolytics/antipsychotics, the effective dosage of the substances active for such treatment will vary according to the particular compound being employed, the severity and nature of condition being treated. Therapy should be initiated at lower doses, the dosage thereafter being increased, if necessary, to produce the desired effect. In general, the compounds of the invention are most desirably administered at a concentration that will generally afford effective results without causing any harmful or deleterious effects.

When the compounds of the invention are employed as anxiolytics/antipsychotic agents, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto on oral administration. The compounds may also be injected parenterally in which case they are used in the form of a sterile solution containing other solutes, for example, enough saline or glucose to make the solution isotonic.

The antipsychotic activity of the compounds of the invention and their substantial lack of extrapyramidal side effects may be demonstrated by standard pharmacological procedures, which are described more fully in the examples given hereafter.

The following examples show the preparation and pharmacological testing of compounds within the invention.

EXAMPLE 1

Hexahydro-2-[4-(4-pyridinyl)butyl]-4,7-epoxy-1,2-benzisothiazol-3(2H)-one 1,1-dioxide, hydrochloride To a stirred solution of 3.0 g (0.14 mol) of hexahydro-4,7-epoxy-1,2-benzisothiazol-3(2H)-one 1,1-dioxide in 50 ml of dimethylformamide are added 4.2 g (0.014 mol) of 4-pyridylbutylbromide hydrobromide, 0.5 g of cesium carbonate and 3 mL of triethylamine. Stirring is continued for 48 hours at room temperature, dimethylformamide is removed under reduced pressure and the residue is extracted with methylene chloride (3×200 mL). The methylene chloride extracts are collected, washed with water, dried (anhydrous $Na_2SO_4$) and evaporated in vacuo. The crude product is purified by HPLC to afford 3.0 g of pure product (61% yield). This is converted to its hydrochloride salt, m.p. 218°–220° C.

Analysis for: $C_{16}H_{20}SN_2O_4.HCl.\frac{1}{2}H_2O$. Calculated: C, 50.32; H, 5.76; N, 7.33. Found: C, 50.55; H, 5.48; N, 7.43.

EXAMPLE 2

Hexahydro-2-[4-]1-(2-pyrimidinyl)-4-piperidinyl]butyl]-4,7-epoxy-1,2-benzisothiazol-3(2H)-one 1,1-dioxide, hydrochloride, monohydrate 2.0 g (0.004 mol) of hexahydro-2-[4-(4pyridinyl)-butyl]-4,7-epoxy-1,2-benzisothiazol-3(2H)-one 1,1-dioxide of Example 1 are hydrogenated overnight in 300 ml of ethanol in the presence of 1 ml of glacial acetic acid and 0.7 g of 5% $Rh/Al_2O_3$.

The catalyst is filtered and solvent is removed to afford the totally reduced product which is dissolved in 50 ml of dimethylformamide and to the stirred solution are added 2 g (0.017 mol) of 2-chloropyrimidine and 4 ml of triethylamine. Stirring is continued overnight and the solvent is evaporated under reduced pressure and the residue is extracted with methylene chloride (3×200 ml). The methylene chloride extracts are collected, washed with water, dried over anhydrous $Na_2SO_4$ and evaporated in vacuo. The remaining oil is subjected to HPLC separation. Evaporation of the solvent from the desired fractions ($R_f$ 0.48 in system of 30% methanol-ethyl acetate) gives 7 g of the title compound as a yellow oil which is converted to the hydrochloride salt; m.p. 214°–216° C.

Analysis for: $C_{20}H_{28}SN_4O_4.HCl.H_2O$. Calculated: C, 50.57; H, 6.53; N, 11.80. Found: C, 50.71; H, 6.53; N, 11.80.

EXAMPLE 3

3a,4,7,7a-Tetrahydro-2-[4-(4-pyridinyl)butyl]-4,7-methano-1,2-benzisothiazol-3(2H)-one 1,1-dioxide, hydrochloride The title compound is prepared following the procedure of Example 1 using 4a,4,7,7a-tetrahydro-4,7-methano-1,2-benzisothiazol-3(2H)-one 1,1-dioxide instead of hexahydro-4,7-epoxy-1,2-benzisothiazol-3(2H)-one 1,1-dioxide and is converted to the hydrochloride salt; m.p. 211°–213° C.

Analysis for: $C_{17}H_{20}SN_2O_3.HCl$. Calculated: C, 55.35; H, 5.69; N, 7.59. Found: C, 55.05; H, 5.74; N, 7.63.

EXAMPLE 4

Hexahydro-2-[4-[1-(6-chloro-2-pyrazinyl)-4-piperidinyl]butyl]-4,7-epoxy-1,2-benzisothiazol-3(2H)-one 1,1-dioxide, hydrochloride, hydrate The title compound is prepared following the procedure of Example 2 using 2,6-dichloropyrazine instead of 2-chloropyrimidine and is and is converted to the hydrochloride salt; m.p.151°–153° C.

Analysis for: $C_{20}H_{25}ClN_4SO_4.HCl.H_2O$. Calculated: C, 50.90; H, 5.93; N, 11.87. Found: C, 50,95; H, 5.87; N, 12.09.

EXAMPLE 5

3a,4,7,7a-Tetrahydro-5,6-dimethyl-2-[4-(4-pyridinyl)butyl]-1,2-benzisothiazol-3(2H)-one 1,1-dioxide, hydrochloride The title compound is prepared following the procedure of Example 1 using 3a,4,7,7a-tetrahydro-5,6-dimethyl-1,2-benzisothiazol-3(2H)-one 1,1-dioxide instead of hexahydro-4,7-epoxy-1,2-benzisothiazol-3(2H)-one 1,1-dioxide and is converted to the hydrochloride salt; m.p. 152°–154° C.

Analysis for: $C_{18}H_{24}N_2SO_3.HCl$. Calculated: C, 56.17; H, 6.50; N, 7.28. Found: C, 56.02; H, 6.44; N, 7.42.

EXAMPLE 6

Hexahydro-2-[4-[1-(2-pyrazinyl)-4-piperidinyl]butyl]-4,7-epoxy-1,2-benzisothiazol-3(2H)-one 1,1-dioxide, hydrochloride, hemihydrate The title compound is prepared following the procedure of Example 2 using 2-chloropyrazine instead of 2-chloropyrimidine and is converted to the hydrochloride salt; m.p. 147°–148° C.

Analysis for: $C_{20}H_{28}N_4SO_4.HCl.\frac{1}{2}H_2O$. Calculated : C, 51.44; H, 6.43; N, 12.00. Found: C, 51.48; H, 5.88; N, 11.47.

EXAMPLE 7

2-[4-(4-Pyridinyl)butyl]-1,2-benzisothiazol-3(2H)-one 1-oxide, hydrochloride

The title compound is prepared following the procedure of Example 1 using 1,2-benzisothiazol-3(2H)-one 1-oxide instead of hexahydro-4,7-epoxy-1,2-benzisothiazol-3(2H)-one 1,1-dioxide and is converted to the hydrochloride salt; m.p. 188°–190° C.

Analysis for: $C_{16}H_{16}N_2O_2S.HCl.\frac{1}{4}H_2O$. Calculated: C, 56.3; H, 5.13; N, 8.21. Found: C, 55.95; H, 5.18; N, 8.31.

EXAMPLE 8

The compounds of the invention are tested in an assay to determine their ability to antagonize apomorphine-induced stereotyped behavior. The assay measures the in vivo dopamine receptor blocking activity of the compounds and provides a means for gauging whether the compounds tested may potentially exhibit extrapyramidal side effects.

The assay is carried out as follows:

20–25 gm male CF-1 mice (Charles River) are used. The mice are tested one week before the experiment for a positive stereotyped response to 10 mg/kg s.c. apomorphine. Test compounds, suspended or solubilized in 0.25% Tween 80 ® in water, are administered at several dose levels to male mice (6/dose level). A control group, run simultaneouly with drug groups, receives equal volumes of solvent. Thirty minutes later (i.p. administration), drug-treated and control mice are challenged with 10 mg/kg apomorphine s.c. Five minutes after the injection, the rearing-head-bobbing-licking syndrome induced by apomorphine is recorded as present or absent for each animal. Readings are repeated every 5 minutes during a 30 minute test session.

The number of positive or negative 5-minute intervals during which apomorphine-induced stereotyped behavior is present or absent is measured. $ED_{50}$ values (with 95% confidence intervals) are calculated for inhibition of apomorphine-induced stereotyped behavior, by a simple linear regression analysis with inverse prediction.

| STANDARD COMPOUNDS: | $ED_{50}$ and 95% confidence interval, mg/kg intraperitoneal |
| --- | --- |
| Haloperidol | 1.37 (0.88–2.34) |
| Chloropromazine | 8.48 (4.79–16.38) |
| Clozapine | 30.06 (19.42–48.21) |

The compounds of the invention and buspirone, when tested in this assay are inactive, evidencing a low potential for exhibiting extrapyramidal side effects, such as pseudoparkinsonism, tardive dyskinesia and the like.

EXAMPLE 9

The compounds of the invention are further studied for their ability to inhibit limbic D-2 dopamine receptor binding. This in vitro assay measures the ability of the compounds tested to bind to the dopamine receptor sites. Those compounds which exhibit a weak binding effect have a low liability to display potential extrapyramidal side effects.

The assay is carried out as follows:

Several rats are decapitated and the brains are rapidly removed. Limbic brain tissue (nucleus accumbens, septal area, olfactory tubercle) is dissected and homogenized on ice in 9 volumes of buffer (50 mM NaCl, 5 mM KCl, 1 mM $CaCl_2$, 1 mM $MgCl_2$, 0.1% L-ascorbic acid, 10 μM pargyline HCl, pH 7.1) using a Polytron homogenizer at setting 5 for three 15-sec bursts. The homogenate is then diluted 4-fold with buffer and centrifuged at 30,000×g for 20 min, and the supernatant is discarded. The pellet is resuspended in the same volume of buffer and recentrifuged as before, again discarding the supernatant. This pellet is then resuspended in the same volume of buffer used in the homogenization, and the protein content of this preparation is assayed by the Lowry method. The homogenate is stored frozen at -70° C. until use.

Thirty μL of the homogenate (0.2-0.3 mg protein/sample) are incubated with 0.3 nM $^3$H-spiroperidol (New England Nuclear) and various concentrations of test drug in a final volume of 1 ml of the above buffer for 10 min in a 37° C. water bath. At the end of the incubation, 3 ml of cold 50 mM Tris-HCl, pH 7.7, are added to each tube, and the contents are rapidly vacuum-filtered through Whatman GF/B glass-fiber filters. The filters are then rapidly washed 3 times with 3 ml of the same buffer, placed in scintillation vials, and shaken for 15 min with 10 ml of Hydrofluor (National Diagnostics) scintillation cocktail. The vials are then counted in a Packard 460CD scintillation counter.

Specific binding is defined as total binding less binding in the presence of 1 μM (+)butaclamol. Binding in the presence of various concentrations of test drug is expressed as a percent of specific binding when no drug is present. These results are then plotted as logit % binding vs. log concentration of test drug. Linear regression analysis then yields a straight line with 95% confidence limits from which an $IC_{50}$ can be inversely predicted. $K_i$ (inhibition constant) for the test drug is then calculated by the formula:

$$K_i = \frac{IC_{50}}{1 + \frac{[^3H-\text{Spiroperidol}]}{K_D}} \text{ where}$$

$K_D$ = 0.3 nM for spiroperidol binding

| STANDARD COMPOUNDS: | $K_i$ and 95% confidence interval |
|---|---|
| Haloperidol | 4.0 (3.0–5.6) nM |
| Clozapine | 34 (23–54) nM |
| Fluphenazine | 4.5 (3.6–5.6) nM |
| Sulpiride | 376 (174–5000) nM |

The results of testing of some of the compounds of the invention, and the prior art compound buspirone (8-[4-[4-(2-pyrimidinyl)-1-piperazinyl]butyl]-8-azaspiro[4.5]decane-7,9-dione) in this assay are presented in Table 1.

TABLE 1

| Compound of Example No. | Limbic D-2 Binding Inhibition |
|---|---|
| Buspirone | 119 |
| 1 | 3% inhibition at 1 μM |
| 2 | 6% inhibition at 1 μM |
| 3 | 1% inhibition at 1 μM |
| 4 | 7% inhibition at 1 μM |
| 5 | 56% inhibition at 1 μM |
| 6 | 6% inhibition at 1 μM |
| 7 | 14% inhibition at 1 μM |

The results show that the compounds of the invention display a very weak effect, evidencing a low potential for extrapyramidal side effects.

EXAMPLE 10

A test designed to determine the potential antipsychotic activity of the compounds of the invention is the conditioned avoidance (shelf-jump response) test.

This test is carried out as follows:

Male CD rats (Charles River) maintained at approximately 400–450 gm body weight are used. Previously trained rats are placed in plexiglass experimental chambers divided into two sections; a main chamber (10½"×6¾"×11⅞" high) and an elevated chamber or shelf (5⅞"×6⅞"×5¾"). A moveable wall, controlled by a motor, determines whether the rat has access to the shelf at any time during the experiment. The experimental chamber also contains a house light and sonalert. A steel grid floor in the main chamber is wired for presentation of electric shock. Each trial consists of a fifteen-second warning tone (conditioned stimulus), continuing for an additional fifteen seconds accompanied by electric shock (unconditioned stimulus). A response (jumping onto the exposed shelf of the upper chamber) occurring during the initial fifteen-second warning tone is considered an avoidance response, while a response occurring during shock delivery is considered an escape response. Trials are presented on a fixed interval schedule of one minute. The session consists of thirty-six trials. Animals are run twice weekly with control sessions always preceding a drug run, and with at least one day intervening. Compounds are administered i.p. or p.o. at appropriate pre-treatment times to a minimum of five rats at each dose level over a range of doses.

The following experimental parameters are recorded by computer: (1) the number of avoidance responses, (2) the number of escape responses, and (3) the number of trials in which no response occurred. These data are used to calculate the percent difference from control values previously determined and are presented for visual comparison via a line graph.

Response counts are summed over all subjects at a given dose. The number of trials in which rats fail to exhibit an avoidance response (Avoidance Block, AB) is determined at each dose. This number is expressed as a percentage of the total trials. Control performance is arbitrarily assigned a value of 100% for avoidance responding and the dose calculated to produce a 50% block in avoidance responding ($AB_{50}$) is obtained from a dose-effect regression line fitted by the method of least squares. Potential antipsychotic compounds suppress avoidance responding and increase escape responding.

| Standard Compounds: | $AB_{50}$ (mg/kg i.p.) |
|---|---|
| Haloperidol | 0.19 |
| Chlorpromazine | 3.69 |
| Clozapine | 6.94 |
| Buspirone | 9.44 |

The results for compounds of this invention in this test are presented in Table 2.

TABLE 2

| Compound of Example No. | Active at mg/kg |
|---|---|
| 1 | 40 (i.p.)* |
| 3 | 40 (i.p.) |

TABLE 2-continued

| Compound of Example No. | Active at mg/kg |
|---|---|
| 5 | 40 (i.p.) |

*(i.p.) = intraperitoneally administered drug

The results show that compounds of the invention are active intraperitoneally in this test.

What is claimed is:

1. A compound having the formula

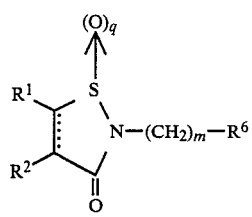

wherein $R^1$ and $R^2$ taken together represent

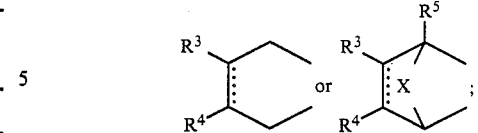

where the dotted lines represent optional double bonds;

$R^3$, $R^4$ and $R^5$ are each, independently, hydrogen, lower alkyl, phenyl or halo;

$R^6$ is 2-pyridinyl or 2-pyridinyl substituted by lower alkyl, lower alkoxy, trifluoromethyl, cyano, nitro or halo;

X is lower alkylene, vinylene, O or NH;

m is 1–5;

q is 1–2;

and the pharmaceutically acceptable salts thereof.

2. The compound of claim 1, having the name hexahydro-2-[4-(4-pyridinyl)butyl]-4,7-epoxy-1,2-benzisothiazol-3(2H)-one 1,1-dioxide.

3. The compound of claim 1, having the name 3a,4,7,7a-tetrahydro-2-[4-(4-pyridinyl)butyl]-4,7-methano-1,2-benzisothiazol-3(2H)-one 1,1-dioxide.

4. The compound of claim 1, having the name 3a,4,7,7a-tetrahydro-5,6-dimethyl-2-[4-(4-pyridinyl)butyl]-1,2-benzisothiazol-3(2H)-one 1,1-dioxide.

* * * * *